United States Patent

Wu et al.

[11] Patent Number: 6,107,311
[45] Date of Patent: Aug. 22, 2000

[54] DIHYDROBENZOFURAN AND RELATED COMPOUNDS USEFUL AS ANTI-INFLAMMATORY AGENTS

[75] Inventors: Laurence Ichih Wu; John Michael Janusz, both of Cincinnati, Ohio

[73] Assignee: The Procter & Gamble Company, Cincinnati, Ohio

[21] Appl. No.: 09/057,685

[22] Filed: Apr. 9, 1998

Related U.S. Application Data

[62] Division of application No. 08/595,113, Feb. 1, 1996, Pat. No. 5,750,543.

[51] Int. Cl.[7] .......................... A61K 31/44; A61K 31/34; C07D 401/06; C07D 407/06
[52] U.S. Cl. .......................... 514/337; 514/365; 514/422; 514/443; 514/444; 514/469; 544/333; 544/405; 546/281.1; 546/282.7; 548/128; 548/131; 548/134; 548/143; 548/200; 548/214; 548/236; 548/248; 548/252; 548/262.2; 548/346.1; 549/58; 549/60; 549/462
[58] Field of Search ........................ 514/337, 365, 514/422, 443, 444, 469; 546/281.1, 282.7; 548/128, 131, 134, 143, 200, 214, 236, 248, 252, 262.2, 346.1; 549/58, 60, 462; 544/333, 405

[56] References Cited

U.S. PATENT DOCUMENTS

| | | | |
|---|---|---|---|
| 4,670,457 | 6/1987 | Doria et al. | 514/470 |
| 4,849,428 | 7/1989 | Dobson et al. | 549/307 |
| 5,262,430 | 11/1993 | Borrevang et al. | 514/337 |

Primary Examiner—Ba K. Trinh
Attorney, Agent, or Firm—Carl J. Roof; Mary Pat McMahon; David L. Suter

[57] ABSTRACT

A compound having the structure:

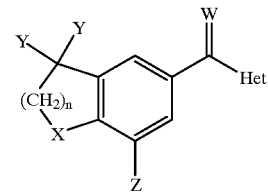

wherein
(a) n is from 1 to about 3;
(b) X is selected from the group consisting of O, S, SO, or $SO_2$;
(c) Y is independently hydrogen or straight, branched or cyclic alkyl having from 1 to about 4 carbon atoms, or the Y's are bonded together to form an alkanyl ring having from about 3 to about 7 atoms;
(d) Z is hydrogen or straight, branched or cyclic alkyl having from 3 to about 10 atoms other than hydrogen;
(e) W is O or S; and
(f) Het is a heteroaryl group comprising one or more rings each ring containing from about 5 to about 6 atoms other than hydrogen and wherein the group contains at least one heteroatom selected from O, N, or S.

pharmaceutical compositions comprising such compounds, and methods of treating inflammation or pain using such compounds.

13 Claims, No Drawings

DIHYDROBENZOFURAN AND RELATED COMPOUNDS USEFUL AS ANTI-INFLAMMATORY AGENTS

This is a divisional of U.S. Ser. No. 08/595,113, filed Feb. 1, 1996 now U.S. Pat. No. 5,750,543.

TECHNICAL FIELD

The subject invention relates to nonsteroidal anti-inflammatory drugs, particularly to substituted dihydrobenzofuran and related compounds.

BACKGROUND OF THE INVENTION

Certain dihydrobenzofuran compounds and other compounds structurally related thereto have been found to have significant disease altering activities. Such compounds, processes for making them, and uses for them are disclosed in the following references: U.S. Pat. No. 4,670,457 issued to Doria, Romeo & Como on Jun. 2, 1987; U.S. Pat. No. 4,849,428 issued to Dobson, Loomans, Matthews & Miller on Jul. 18, 1989; Japanese Patent Publication No. 53-005178 of Yoshitomi Pharm. Ind. KK published Jan. 1, 1978; Hammond, M. L., I. E. Kopka, R. A. Zambias, C. G. Caldwell, J. Boger, F. Baker, T. Bach, S. Luell & D. E. MacIntyre, "2,3-Dihydro-5-benzofuranols as Antioxidant-Based Inhibitors of Leukotriene Biosynthesis", *J. Med. Chem.*, Vol 32 (1989), pp. 1006–1020; Ortiz de Montellano, P. R & M.A. Correia, "Suicidal Destruction of Cytochrome P-450 during Oxidative Drug Metabolism", *Ann. Rev. Pharmacol. Toxicol.*, Vol 23 (1983), pp. 481–503; Chalorabarti, J. K., R.J. Eggleton, P. T. Gallagher, J. Harvey, T. A. Hicks, E. A. Kitchen, and C. W. Smith, "5-Acyl-3-substituted-benzofuran-2(3H)-ones as Potential Anti-inflammatory Agents", *J. Med. Chem.*, Vol 30 (1987), pp. 1663–1668.

It is an object of the subject invention to provide compounds which have effective anti-inflammatory, analgesic and/or anti-oxidant activity.

It is a further object of the subject invention to provide such compounds which cause few adverse side effects.

It is also an object of the subject invention to provide methods for treating inflammation and/or pain using the subject compounds.

SUMMARY OF THE INVENTION

The subject invention compounds having the structure:

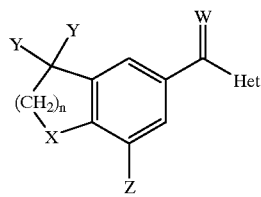

wherein (a) n is from 1 to about 3;

(b) X is selected from the group consisting of O, S, SO, or $SO_2$;

(c) Y is independently hydrogen or straight, branched or cyclic alkyl having from 1 to about 4 carbon atoms, or the Y's are bonded together to form an alkanyl ring having from about 3 to about 7 atoms;

(d) Z is hydrogen or straight, branched or cyclic alkyl having from 3 to about 10 atoms other than hydrogen;

(e) W is O or S; and (f) Het is a heteroaryl group comprising one or more rings each ring containing from about 5 to about 6 atoms other than hydrogen and wherein the group contains at least one heteroatom selected from O, N, or S.

DETAILED DESCRIPTION OF THE INVENTION

As used herein, unless otherwise indicated, "alkyl" or "alkanyl" means a straight, branched or cyclic hydrocarbon chain, saturated or unsaturated, unsubstituted or substituted. Preferred alkyl are $C_1$–$C_{10}$; more preferred are $C_1$–$C_8$; especially preferred are $C_1$–$C_2$. Preferred alkyl are straight chain. Preferred branched alkyl have one or two branches, preferably one branch. Preferred cyclic alkyl are monocyclic. Preferred alkyl are saturated. Preferred alkyl are unsubstituted. Preferred substituted alkyl are mono-, di-, or trisubstituted, more preferably monosubstituted. Preferred alkyl substituents include halo, hydroxy, oxo, alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl (e.g., piperidinyl, tetrahydrothienyl, pyrrolidinyl, piperazinyl, morpholinyl, thiomorpholinyl, tetrahydropyranyl, tetrahydrothiopyranyl, tetrahydrofuranyl, imidazolidinyl, pyrazolidinyl, oxazolidinyl, isoxazolidinyl, thiazolidinyl, isothiazolidinyl, azapinyl, oxepinyl, thiepinyl, triazolidinyl, tetrazolidinyl), heteroaryl, amino (e.g., amino, mono- and di- $C_1$–$C_3$ alkanylamino, methylphenylamino, methylbenzylamino, $C_1$–$C_3$ alkanylamido, carboxamido, ureido, N'-alkylureido, N',N'-dialkylureido, N',N',N-trialkylureido, guanidino, N'-alkylguanidino, N',N'-dialkylguanidino, or alkoxy carbonyl.

As used herein, "alkoxy" means —O-alkyl.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include hydroxy, mercapto, halo, methyl, ethyl and propyl.

As used herein, "heteraryl" means a moiety having one or more rings each ring having 5 or 6 ring atoms including from 1 to 6 carbon atoms and at least one ring contains from 1 to 4 heteroatoms selected from O, S and N. Preferred heteroaryls have 1 or 2 heteroatoms in the ring, also preferably 1 heteroatom in the ring. Specific preferred heteroaryls include 2 or 3-furyl, 2 or 3-thienyl, 2 or 3-pyrrolyl either unsubstituted or alkylsubstituted on nitrogen, 2, 4, or 5 thiazolyl, 2, 4, or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxdiazolyl, 2 or 5-thiadiazolyl, triazolyl, tetrazolyl, pyridyl, pyrimidinyl, pyrazinyl, indolyl, quinolyl, isoquinolyl, imidazothiazolinyl, imidazopyidinyl, imidazoimidazolinyl. Heteraryls are unsubstituted or substituted, preferably unsubstituted. Preferred substituted heteraryls are mono-, di-, or trisubstituted, more preferably monosubstituted. Preferred heteroaryl substituents include alkyl, halo, hydroxy, alkoxy, thio, nitro, amino, amido, ureido, guanidino, thiocarbamamido, thioureido.

As used herein, "halo" means fluoro, chloro, bromo or iodo. Preferred halo are fluoro, chloro and bromo; more preferred are chloro and bromo, especially chloro.

Compounds

The subject invention involves compounds having the following structure:

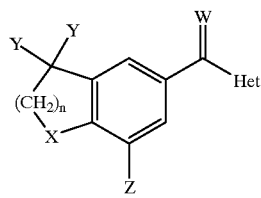

wherein
(a) n is from 1 to about 3;
(b) X is selected from the group consisting of O, S, SO, or $SO_2$;
(c) Y is independently hydrogen or straight, branched or cyclic alkyl having from 1 to about 4 carbon atoms, or the Y's are bonded together to form an alkanyl ring having from about 3 to about 7 atoms;
(d) Z is hydrogen or straight, branched or cyclic alkyl having from 3 to about 10 atoms other than hydrogen;
(e) W is O or S; and
(f) Het is a heteroaryl group comprising one or more rings each ring containing from about 5 to about 6 atoms other than hydrogen and wherein the group contains at least one heteroatom selected from O, N, or S.

In the above structure, each Y is independently selected from hydrogen, straight or branched alkanyl having from 1 to about 4 carbon atoms, and cyclic alkyl having about 3 carbon atoms, cyclopropyl, or the Y's are bonded together to form an unsubstituted cyclic alkanyl ring having from 3 to about 7 carbon atoms in the ring. Each Y is preferably hydrogen, methyl, ethyl or cyclopropyl; more preferably hydrogen or methyl; most preferably methyl. Preferably both Y's are the same. When the Y's are bonded together to form a cyclic ring, the ring is preferably cyclopropyl, cyclobutyl or cyclopentyl, more preferably cyclopropyl.

In the above structure, Z is selected from branched or cyclic alkyl, and unsubstituted or alkanyl-substituted phenyl, or benzyl, Z having from 3 to about 10 atoms other than hydrogen. Z is preferably saturated. Z is preferably branched alkanyl having from about 3 to about 8 carbon atoms, more preferably from about 4 to about 6 carbon atoms. Z is preferably branched alkanyl having 2 or more branches, more preferably 2 branches. Preferred branched alkanyl Z include t-butyl, neopentyl, isopropyl; most preferred is t-butyl. Preferred cyclic alkanyl Z include cyclopropyl, cyclobutyl, cyclopentyl, cyclohexyl, cycloheptyl. Also preferred cyclic alkanyl Z include methyl or ethyl with a terminal cyclopropyl, cyclobutyl or cyclopentyl, especially cyclopropylmethyl or cyclopropylethyl. Also preferred Z is unsubstituted phenyl or benzyl.

In the above structure, Het is selected from the group consisting of 2 or 3-furyl, 2 or 3-thienyl, 2 or 3-pyrrolyl either unsubstituted or alkyl substituted on nitrogen, 2, 4, or 5-thiazolyl, 2 or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxdiazolyl, 2 or 5-thiadiazolyl, triazolyl, tetrazolyl, pyridyl, pyrimidinyl, pyrazinyl, indoyl, quinolyl, isoquinolyl, imidazothiazolinyl, imidazopyridinyl, imidazopyridinyl, imidazoimidazolinyl.

Preferred compounds of the subject invention are included in the following table:

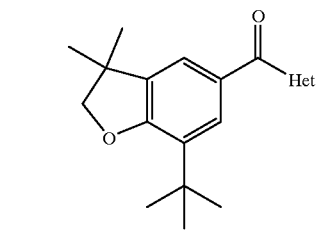

| Compound No. | Het |
|---|---|
| 1 | 2-furyl |
| 2 | 5-methyl-2-furyl |
| 3 | 3-furyl |
| 4 | 2-thienyl |
| 5 | 5-nitro-2-thienyl |
| 6 | 3-thienyl |
| 7 | N-methyl-2-pyrrolyl |
| 8 | 2-thiazolyl |
| 9 | 2-pyridyl |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Anti-inflammatory Activity of Antioxidants", *Anti-inflammatory and Antirheumatic Drugs*, Vol. III, chapter 4, K. D. Rainsford, ed., CRC Press, Inc. (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1985), pp. 332–339; Sellye, H., "Further Studies Concerning the Participation of the Adrenal Cortex in the Pathogenesis of Arthritis", *British Medical Journal,* Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine,* Vol. 111 (1982), pp. 544–547; Otterness, I., & M. L. Blivan, "Laboratory Methods for Testing Nonsteroidal Antiinflammatory Drugs", *Nonsteroidal Antiinflammatory Drugs,* Chapter 3, J. G. Lombardino, ed., John Wiley & Sons, Inc. (1985), pp. 111–252. Hitchens, J. T., S. Goldstein, L. Shemano & J. M. Beiler, "Analgesic Effects of Irritants in Three Models of Experimentally-Induced Pain", *Arch, Int. Pharmacodyn.,* Vol 169, No. 2 (1987) pp. 384–393; Milne, G. M. & T. M. Twomey, "The analgesic Properties of Piroxicam in Animals and Correlation with Experimentally Determined Plasma Levels", *Agents and Actions,* Vol 10 , No. 1/2 (1980), pp. 31–37; Randall, L. O. & J. J. Selitto, "A Method for Measurement of Analgesic Activity of Inflamed Tissue", *Arch. Int. Pharmacodyn., Vol.* 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.,* Vol. 148, No. 3 (1985), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs. Some compounds of the subject invention are even gastroprotective, protecting the stomach and intestines from ulcers and erosions, particularly those caused by ethanol or other NSAIDs.

Certain NSAIDs, when dosed systematically, cause an undesirable increase in systemic levels of certain liver enzymes. Compounds of the subject invention generally cause little or no liver enzyme side effects.

Compounds useful in the subject invention can be made using the following general reaction scheme:

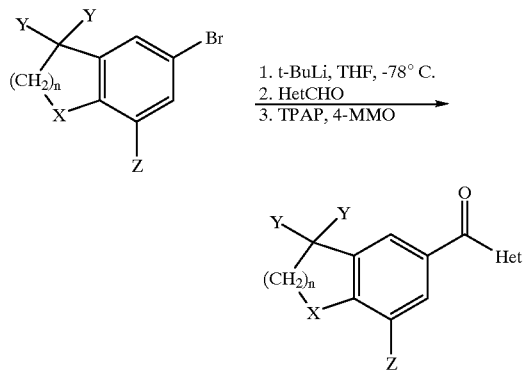

The heterocyclic ketones can be converted to the corresponding thioketones by reaction with Lawesson's reagent.

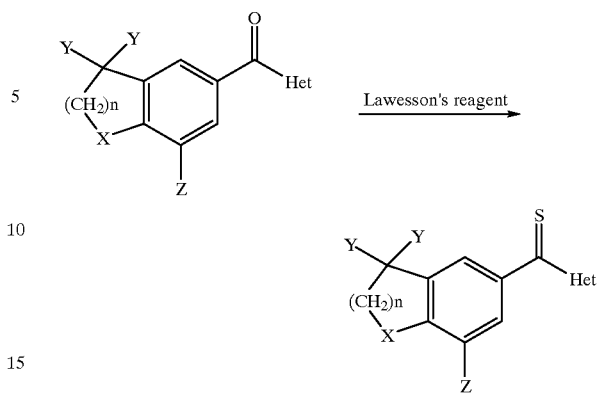

The 2,3-dihydro-3,3-dimethylbenzofuran/thiophene heterocyclic ketones can be prepared in a two-step procedure involving reaction of the 5-lithio derivative shown with heterocyclic aldehydes followed by oxidation with tetrapropylammonium perruthenate and 4-methylmorpholine-N-oxide.

SYNTHESIS EXAMPLES

The following non-limiting examples provide further information regarding synthesis of the subject compounds.

Example 1

7-tert-Butyl-2,3-dihydro-3,3-dimethyl-5-(2-furoyl)benzo[b]furan t-Butyllithium (5.5 mL, 9.4 mmol, 1.7 M in pentane) is added dropwise to a solution of 5-bromo-7-tert-butyl-2,3-dihydro-3,3-dimethylbenzo[b]furan (1.13 g, 4.0 mmol) in 16 mL of anhydrous THF at −78° C.; the resulting yellow solution is stirred at −78° C. for 10 min and 2-furaldehyde (0.50 mL, 6.0 mmol) is introduced. The reaction mixture is warmed to 0° C., stirred for 30 min, quenched with water, and extracted with ether. The extract is dried over anhydrous magnesium sulfate and concentrated to give 1.55 g of an oily residue, which is dissolved in 25 mL of dichloromethane and reacted for 2 h with 4-methylmorpholine N-oxide (0.90 g, 7.7 mmol) and tetrapropylammonium perruthenate (0.16 g, 0.46 mmol). The reaction mixture is filtered through a short column of silica gel and concentrated to yield 1.57 g of the crude product. Purification by flash column chromatography on silica gel (2.5%–>4% ethyl acetate-hexane) gives about 1.0 g (84%) of the title compound as a colorless solid: mp 103–104° C.

Example 2

2,3-Dihydro-3,3-dimethyl-7-tert-butyl-5-(5-methyl-2-furoyl)benzo[b]furan

To an oven-dried three necked 100 mL round bottom flask were added 2,3-dihydro-3,3-dimethyl-7-tert-butyl-5-bromobenzofuran (1.2 g; 4.24 mmol) and anhydrous THF (17 mL). The solution is cooled to −78 C. in a dry ice/acetone bath. While stirring, n-butyllithium, 2.5 M solution in hexane (1.7 mL; 4.24 mmol) is added dropwise at that temperature. After the addition, the clear yellow solution is stirred for 10 min. The 5-methylfurfural (0.34 mL; 3.4 mmol) was added. The reaction mixture is stirred at 0 C. for 0.5 h, and the course of the reaction is monitored by TLC analysis. The TLC indicates that the reaction is complete and so the reaction mixture was quenched with 10 mL of distilled water. The mixture is extracted with ethyl acetate (3×50 mL) and brine (50 mL). The organic layer is dried over $MgSO_4$, filtered, and concentrated under reduced pressure to give a yellow oil. The oil is stirred with anhydrous dichloromethane (27 mL) at room temperature. While stirring, tetrapropylammonium perruthenate(VII) (0.17 g; 0.50 mmol) and 4-methylmorpholine-N-oxide (0.95 g; 8.16 mmol) are added. A dark brown precipitate is formed. The mixture is stirred for 2.5 h at room temperature. The reaction mixture is filtered through a bed of silica, washed with dichloromethane, and concentrated under reduced pressure to afford about 1.37 g of a brown oil. The brown oil is purified by silica gel column chromatography (30 g $SiO_2$) using elution solvents of hexane/ethyl acetate (5:1) (900 mL) and hexane/ethyl acetate (3:1) (600 mL). The desired fractions are collected, combined and concentrated under reduced pressure to afford orange powder; however, the analytical data may indicate that the compound is about 95% pure so the compound is repurified with the same amount of silica gel and solvents to afford a light orange powder, which is dried under high vacuum in the presence of $P_2O_5$ for 48 h to yield 315.4 mg (45.5%) of the desired product. Using TLC analysis with normal phase plates, the product, detected under UV light and sulfuric acid/ethanol (5:95) spray, exhibits an $R_f$ of 0.5 using a mobile phase system of hexane/ethyl acetate (3:1): mp 101–104° C;

Example 3

7-tert-Butyl-2,3-dihydro-3,3-dimethyl-5-(3-furoyl) benzo[b]furan t-Butyllithium (5.5 mL, 9.4 mmol, 1.7 M in pentane) is added dropwise to a solution of 5-bromo-7-tert-butyl-2,3-dihydro-3,3-dimethylbenzo[b]furan (1.13 g, 4.0 mmol) in 16 mL of anhydrous THF at −78° C.; the resulting yellow solution is stirred at −78° C. for 10 min and 3-furaldehyde (0.52 mL, 6.0 mmol) is introduced. The reaction mixture is warmed to 0° C., stirred for 30 min, quenched with water, and extracted with ether. The extract is dried over anhydrous magnesium sulfate and concentrated to give 1.53 g of an oily residue, which is dissolved in 25 mL of dichloromethane and reacted for 2 h with 4-methylmorpholine N-oxide (0.90 g, 7.7 mmol) and tetrapropylammonium perruthenate (0.16 g, 0.46 mmol). The reaction mixture is filtered through a short column of silica gel and concentrated to yield 1.43 g of the crude product. Purification by flash column chromatography on silica gel (2.5% ethyl acetate-hexane) gives about 0.80 g (67%) of the title compound as a colorless solid: mp 120–121° C.

Example 4

7-tert-Butyl-2,3-dihydro-3,3-dimethyl-5-(2-thenoyl) benzo[b]furan t-Butyllithium (4.6 mL, 7.8 mmol, 1.7 M in pentane) is added dropwise to a solution of 5-bromo-7-tert-butyl-2,3-dihydro-3,3-dimethylbenzo[b]furan (1.0 g, 3.5 mmol) in 15 mL of anhydrous ether at −78° C.; the resulting yellow solution is stirred at −78° C. for 10 min and 2-thiophenecarboxaldehyde (0.49 mL, 5.3 mmol) was introduced. The reaction mixture is kept at −78° C. for 15 min, warmed to −20° C., quenched with water, and warmed to room temperature. The ethereal layer is dried over anhydrous magnesium sulfate and concentrated to provide about 1.44 g of a brownish oil, which is dissolved in 20 mL of dichloromethane and reacted for 18 h with 4-methylmorpholine N-oxide (0.47 g, 4.0 mmol) and tetrapropylammonium perruthenate (0.14 g, 0.4 mmol). The reaction mixture is filtered through a short column of silica gel, washed with aqueous sodium bisulfite solution, dried over anhydrous magnesium sulfate, and concentrated in vacuo. Purification of the residue by flash column chromatography on silica gel (10% ethyl acetate-hexane) gives about 0.81 g (74%) of the title compound as a light yellow solid: mp 103–105° C.

Example 5

2,3-dihydro-3,3-dimethyl-7-tert-butyl-5-(5-nitro-2-thiophenecarbonyl)-benzo[b]furan To an oven-dried three-necked 50 mL round bottom flask are added 2,3-dihydro-3,3-dimethyl-7-tert-butyl-5-bromobenzo[b]furan (1436 mg; 5 mmol) and anhydrous THF (35 mL). The reaction mixture is stirred under nitrogen. The solution was cooled to −78° C. in a dry ice/acetone bath. While stirring, a 2.5 M solution of n-butyllithium in hexane (2.5 mL; 6.36 mmol) is added dropwise at that temperature. After the addition, the clear yellow solution is stirred for 10 min. The 5-nitro-2-thiophenecarboxaldehyde (824.0 mg; 5.24 mmol) is added. The reaction mixture is stirred at 0° C. for 2 h, and the course of the reaction is monitored by TLC analysis. The TLC indicated that the reaction is complete and so the reaction mixture is quenched with distilled water (20 mL). The mixture is extracted with ethyl acetate (5×50 mL) and brine (50 mL). The organic layer is dried over $MgSO_4$, filtered, and concentrated under reduced pressure to yield a dark colored crude product (2.35 g). The crude product is purified by silica gel column chromatography (100 g of $SiO_2$) using an elution solvent of hexane/ethyl acetate (8:1). The desired product is collected and concentrated under reduced pressure to yield a viscous dark oil. This oil is stirred with anhydrous dichloromethane (20 mL) at room temperature. While stirring, tetrapropylammonium perruthenate(VII) (191 mg; 0.53 mmol) and 4-methylmorpholine-N-oxide (991 mg; 8.42 mmol) are added. A green coloration is observed. The mixture is stirred for 1.5 h at room temperature. The reaction mixture is filtered through a bed of silica, eluted with dichloromethane, and concentrated under reduced pressure to afford 200 mg of a dark oil. The oil is purified by preparative TLC chromatography using hexane/ethyl acetate (3:1) as the mobile phase. The desired band is eluted and concentrated under reduced pressure to afford 155 mg of a brown solid; however, the analytical data may indicate that the compound is about 95% pure so the compound is repurified using preparative TLC with dichloromethane as the mobile phase. The desired band is eluted with dichloromethane and concentrated under reduced pressure to afford a yellow solid, which is dried under high vacuum in the presence of $P_2O_5$ for 2 days to yield 92 mg (50.5%) of the desired product. Using TLC analysis with normal phase plates, the product, detected under UV light and sulfuric acid/ethanol (5:95) spray, exhibits an $R_f$ of 0.48 using a mobile phase system of hexane/ethyl acetate (3:1): mp 135–137° C.

Example 6

7-tert-Butyl-2,3-dihydro-3,3-dimethyl-5-(3-thenoyl) benzo[b]furan t-Butyllithium (5.5 mL, 9.4 mmol, 1.7 M in pentane) is added dropwise to a solution of 5-bromo-7-tert-butyl-2,3-dihydro-3,3-dimethylbenzo[b]furan (1.13 g, 4.0 mmol) in 16 mL of anhydrous THF at −78° C.; the resulting yellow solution is stirred at −78° C. for 10 min and 3-thiophenecarboxaldehyde (0.53 mL, 6.0 mmol) was introduced. The reaction mixture is warmed to 0° C., stirred for 10 min, quenched with water, and extracted with ether. The extract is dried over anhydrous magnesium sulfate and concentrated to give about 1.86 g of an oily residue, which is dissolved in 25 mL of dichloromethane and reacted for 1.5 h with 4-methylmorpholine N-oxide (0.94 g, 8.0 mmol) and tetrapropylammonium perruthenate (0.13 g, 0.37 mmol). The reaction mixture is filtered through a short column of silica gel and concentrated to yield 1.79 g of the crude product. Purification by flash column chromatography on silica gel (3% ethyl acetate-hexane) furnishes about 1.01 g (80%) of the title compound as a colorless solid: mp 89–90° C.

Example 7

7-tert-Butyl-2,3-dihydro-3,3-dimethyl-5-[2-(N-methylpyrroloyl)]benzo[b]furan n-Butyllithium (1.6 mL, 4.0 mmol, 2.5 M in hexane) is added to a solution of 5-bromo-7-tert-butyl-2,3-dihydro-3,3-dimethylbenzo[b]furan (1.13 g, 4.0 mmol) in 16 mL of anhydrous THF at −78° C.; the resulting solution is stirred at −78° C. for 10 min and 1-methyl-2-pyrrolecarboxaldehyde (0.34 mL, 3.2 mmol) is introduced. The reaction mixture is warmed to 0° C., stirred for 30 min, quenched with water, warmed to room temperature, and extracted with ethyl acetate; the extract is dried over anhydrous sodium sulfate and concentrated to give about 1.47 g of a purple residue, which is dissolved in 25 mL of dichloromethane and immediately reacted for 2 h with 4-methylmorpholine N-oxide (0.90 g, 7.7 mmol) and tetrapropylammonium perruthenate (0.16 g, 0.46 mmol). The reaction mixture is filtered through a short column of silica gel and concentrated in vacuo. Purification of the residue by flash chromatography on silica gel (5% ethyl acetate-hexane) gives about 0.58 g (47%) of the title compound as a brownish oil.

Example 8

7-tert-Butyl-2,3-dihydro-3,3-dimethyl-5-(2-thiazoloyl)benzo[b]furan t-Butyllithium (5.5 mL, 9.4 mmol, 1.7 M in pentane) is added dropwise to a solution of 5-bromo-7-tert-butyl-2,3-dihydro-3,3-dimethylbenzo[b]furan (1.13 g, 4.0 mmol) in 16 mL of anhydrous THF at −78° C.; the resulting yellow solution is stirred at −78° C. for 10 min and 2-thiazolecarboxaldehyde (0.69 mL, 6.0 mmol) is introduced. The dark green reaction mixture is warmed to 0° C., stirred for 30 min, quenched with water, and extracted with ether. The extract is dried over anhydrous magnesium sulfate and concentrated to give about 1.44 g of an oily residue, which was dissolved in 25 mL of dichloromethane and reacted for 18 h with 4-methylmorpholine N-oxide (0.90 g, 7.7 mmol) and tetrapropylammonium perruthenate (0.16 g, 0.46 mmol). The reaction mixture is filtered through a short column of silica gel and concentrated to yield about 1.57 g of the crude product. Purification by flash column chromatography on silica gel (2.5% ethyl acetate-hexane) gives about 0.29 g (23%) of the title compound as an off-white solid: mp 101–103° C.

Example 9

(2-Pyridinyl)-(7-tert-butyl-2,3-dihydro-3,3-dimethylbenzo[b]furan-5-yl) ketone To 1.0 g (3.5 mmol) of a stirring solution of 5-bromo-2,3-dihydro-3,3-dimethylbenzo[b]furan in 2.0 mL of ether and 18 mL of dry hexane at −78° C. is added 4.4 mL (7.1 mmol) of t-butyllithium in hexane. The resulting mixture is stirred for 40 min, then 0.5 g (4.6 mmol) of 2-pyridinecarboxaldehyde is added. The reaction is allowed to slowly reach RT and is then quenched with water. The reaction is then diluted with 50 mL of ether, and the organic layer is separated. The remaining aqueous layer is extracted with ether (3×20 mL). The organic layers are then combined, dried over MgSO$_4$, filtered, and the solvent was removed in vacuo. The residue is dissolved in 20 mL CH$_2$Cl$_2$, and to this solution was added 0.1 g (0.4 mmol) of tetrapropylammonium perruthinate followed by 0.6 g (5.3 mmol) of N-methyl morpholine-N-oxide at RT. The reaction is stirred for 3 h, then filtered through silica gel, and the solvent is removed in vacuo. Purification by sgc with 1 ethyl acetate:5 hexane resultes in about 0.30 g (29%) of a yellow solid. mp 95–97° C.

Example 10

7-tert-Butyl-2,3-dihydro-3,3-dimethyl-5-(2-furoyl)benzo[b]thiophene t-Butyllithium (5.5 mL, 9.4 mmol, 1.7 M in pentane) is added dropwise to a solution of 5-bromo-7-tert-butyl-2,3-dihydro-3,3-dimethylbenzo[b]thiophene (1.20 g, 4.0 mmol) in 16 mL of anhydrous THF at −78° C.; the resulting yellow solution is stirred at −78° C. for 10 min and 2-furaldehyde (0.50 mL, 6.0 mmol) is introduced. The reaction mixture is warmed to 0° C., stirred for 30 min, quenched with water, and extracted with ether. The extract is dried over anhydrous magnesium sulfate and concentrated to give 1.55 g of an oily residue, which is dissolved in 25 mL of dichloromethane and reacted for 2 h with 4-methylmorpholine N-oxide (0.90 g, 7.7 mmol) and tetrapropylammonium perruthenate (0.16 g, 0.46 mmol). The reaction mixture is filtered through a short column of silica gel and concentrated to yield 1.57 g of the crude product. Purification by flash chromatography on silica gel (2.5%–>4% ethyl acetate-hexane) gives about 1.0 g (80%) of the title compound as a solid.

Example 11

7-tert-Butyl-2,3-dihydro-3,3-dimethyl-5-(2-furylthiocarbonyl)benzo[b]furan 7-tert-Butyl-2,3-dihydro-3,3-dimethyl-5-(2-furoyl)benzo[b]furan (600 mg, 2 mmol) and Lawesson's reagent (404 mg, 1 mmol) in dry toluene (10 mL) is refluxed in an argon atmosphere. The mixture is cooled and the toluene evaporated. The resulting solid was purified by flash chromatography on silica gel to give 502 mg (80%) of the title compound as a yellowish crystals.

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from about 0.5% to about 10%, also preferably from about 5 mg to about 3500 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by a person skilled in the art.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. No. 5,189,066 of Kelm & Bruns, issued Feb. 23, 1993, entitled "Pharmaceutical Compositions of Tebufelone", and U.S. Pat. No. 5,281,420 of Kelm & Dobrozsi, issued Jan. 25, 1994, entitled "Solid Dispersion Compositions of Tebufelone", hereby incorporated herein by reference.

Methods

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract, (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for preventing oxidative damage at inflammatory sites by administering a safe and effective amount of a subject compound to a human or lower animal in need of such treatment. While not limited to a particular mechanism, it is believed that the subject compounds inhibit leukotriene synthesis, thereby decreasing neutrophil accumulation at an inflammatory site.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by administration of preferred subject compounds.

Appropriate tests for determining the gastrointestinal safety or gastroprotective or gastric healing properties of the subject compounds are known.

Methods for determining acute gastrointestinal safety are disclosed and/or referred to in the following references:

Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; and Segawa, Y, O. Ohya, T. Abe, T. Omata, et al., "Anti-inflammatory, Analgesic, and Antipyretic Effects and Gastrointestinal Toxicity of the New Anti-inflammatory Drug N-(3-[3-(piperidinylmethyl)phenoxy] propyl)-carbamoylmethylthio)ethyl 1-(p-chlorobenzoyl) 5-Methoxy-2methyl-3-indolylacetate", *Arzneim.-Forsch./Drug Res.*, Vol 42 (1992), pp. 954–992. In the methods disclosed therein, stomachs of the animals are typically examined two hours after dosing a compound. Methods for determining subchronic gastrointestinal safety are disclosed and/or referred to in the following references: Melarange, R., C. Gentry, et al., "Anti-inflammatory and Gastrointestinal Effects of Nabumetone or its Active Metabolite, 6-Methoxy-2-naphthylacetic Acid (6MNA)", *Dig. Dis. Sci.*, Vol. 37 (1992), pp. 1847–1852; and Wong, S., S. J. Lee, et al., "Antiarthritic Profile of BF-389-A Novel Anti-inflammatory Agent With Low Ulcerogenic Liability", *Agents Actions*, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indometharin-induced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm$^2$ to about 200 mg/cm$^2$ of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

Compositions and Method Examples

The following non-limiting examples illustrate the subject invention.

Example A
Pharmaceutical compositions in the form of tablets are prepared by conventional methods, such as mixing and direct compaction, formulated as follows:

| Ingredient | Quantity (mg per tablet) |
| --- | --- |
| Compound 1 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Example B
A pharmaceutical composition in capsule form is prepared by conventional methods, formulated as follows:

| Ingredient | Quantity (mg per capsule) |
| --- | --- |
| Compound 4 | 200 |
| Lactose | To fill to volume of capsule |

The above capsule administered orally once a day substantially reduces the symptomology of a patient afflicted with rheumatoid arthritis or osteoarthritis.

Example C
A pharmaceutical composition in liquid form is prepared by conventional methods, formulated as follows:

| Ingredient | Quantity |
| --- | --- |
| Compound 7 | 200 mg |
| EtOH | 4 ml |
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis of osteoarthritis.

Example D
A pharmaceutical composition in liquid form is prepared by conventional methods, formulated as follows:

| Ingredient | Quantity |
| --- | --- |
| Microcrystalline (micronoized) Compound 9 | 200 mg |
| Avicel (microcrystalline cellulose) | 50 mg |
| Tween 80 | 1.6 ml |
| Methyl cellulose | 0.4 mg |
| Deionized water | 80 ml |

50 ml of the above composition administered perorally twice a day substantially reduces the symptoms of a patient afflicted with rheumatoid arthritis or osteoarthritis.

What is claimed is:

1. A compound having the structure:

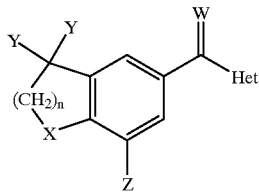

wherein
(a) n is 2 or 3;
(b) X is selected from the group consisting of O, S, SO, or SO$_2$;
(c) Y is independently hydrogen or straight, branched or cyclic alkyl having from 1 to about 4 carbon atoms, or the Y's are bonded together to form an alkanyl ring having from about 3 to about 7 atoms;
(d) Z is hydrogen or straight, branched or cyclic alkyl having from 3 to about 10 atoms other than hydrogen;
(e) W is O or S; and
(f) Het is a heteroaryl group comprising one or more rings each ring containing from about 5 to about 6 atoms other than hydrogen and wherein the group contains at least one heteroatom selected from O, N, or S.

2. The compound of claim 1 wherein X is oxygen or sulphur and W is oxygen.

3. The compound of claim 2 wherein each Y is independently selected from the group consisting of hydrogen, methyl and ethyl; and Z is selected from the group consisting of hydrogen, C$_4$–C$_6$ branched alkanyl having 2 branches, C$_3$–C$_6$ cycloalkanyl, and phenyl.

4. The compound of claim 3 wherein X is oxygen, both Y are methyl, and Z is t-butyl.

5. The compound of claim 3 wherein Het is selected from the group consisting of 2 or 3-furyl, 2 or 3-thienyl, 2 or 3-pyrrolyl either unsubstituted or alkyl substituted on nitrogen, 2, 4, or 5 thiazolyl, 2 or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxadiazolyl, 2 or 5-thiadiazolyl, triazolyl, tetrazolyl, pyridyl, pyrimidinyl, pyrazinyl, indolyl, quinolyl, isoquinolyl, imidazothiazolinyl, imidazopyridinyl, or imidazoimidazolinyl.

6. The compound of claim 5 wherein X is oxygen, and Het is selected from the group consisting of 2-furyl; 5-methyl-2-furyl; 3-furyl; 2-thienyl; 5-nitro-2-thienyl; 3-thienyl; N-methyl-2-pyrrolyl; 2-thiazolyl; or 2-pyridyl.

7. The compound of claim 6 wherein both Y are methyl, and Z is t-butyl.

8. A composition comprising a compound of claim 1 and a pharmaceutically-acceptable carrier.

9. A method of treating inflammation or pain comprising administration, to a human or lower animal in need of such treatment, of a safe and effective amount of a compound of claim 1.

10. A method of treating arthritis comprising daily peroral administration, to a human in need of such treatment, of from about 1 mg/kg to about 20 mg/kg of a compound of claim 1.

11. A composition comprising a compound of claim 7 and a pharmaceutically-acceptable carrier.

12. A method of treating inflammation or pain comprising administration, to a human or lower animal in need of such treatment, of a safe and effective amount of a compound of claim 7.

13. A method of treating arthritis comprising daily peroral administration, to a human in need of such treatment, of from about 1 mg/kg to about 20 mg/kg of a compound of claim 7.

* * * * *